(12) United States Patent
Krivitski et al.

(10) Patent No.: US 6,718,190 B2
(45) Date of Patent: Apr. 6, 2004

(54) SENSOR CALIBRATION AND BLOOD VOLUME DETERMINATION

(75) Inventors: Nikolai M. Krivitski, Ithaca, NY (US); Dimitry M. Starostin, Ithaca, NY (US)

(73) Assignee: Transonic Systems, Inc., Ithaca, NY (US)

( * ) Notice: Subject to any disclaimer, the term of this patent is extended or adjusted under 35 U.S.C. 154(b) by 0 days.

(21) Appl. No.: 10/314,817

(22) Filed: Dec. 9, 2002

(65) Prior Publication Data

US 2003/0130570 A1 Jul. 10, 2003

Related U.S. Application Data

(60) Continuation-in-part of application No. 09/528,880, filed on Mar. 20, 2000, now Pat. No. 6,493,567, which is a division of application No. 08/950,244, filed on Oct. 14, 1997, now Pat. No. 6,041,246.

(51) Int. Cl.$^7$ .................................................. A61B 5/00
(52) U.S. Cl. ...................................................... 600/322
(58) Field of Search ................................. 600/310, 320, 600/322, 481, 504; 604/4.01, 5.01, 6.08; 356/39, 432, 441, 442

(56) References Cited

U.S. PATENT DOCUMENTS

| 3,830,569 A | 8/1974 | Meric |
|---|---|---|
| 4,243,883 A | 1/1981 | Schwarzmann |
| 4,303,336 A | 12/1981 | Cullis |
| 4,484,135 A | 11/1984 | Ishihara et al. |
| 4,515,165 A | 5/1985 | Carroll |
| 4,745,279 A | 5/1988 | Karkar et al. |
| 4,776,340 A | 10/1988 | Moran et al. |
| 4,819,752 A | 4/1989 | Zelin |
| 5,048,524 A | 9/1991 | Bailey |
| 5,066,859 A | 11/1991 | Karkar et al. |
| 5,149,503 A | 9/1992 | Kohno et al. |
| 5,190,040 A | 3/1993 | Aoyagi |
| 5,195,963 A | 3/1993 | Yafuso et al. |
| 5,331,958 A | 7/1994 | Oppenheimer |
| 5,510,716 A | 4/1996 | Buffaloe, IV et al. |
| 5,510,717 A | 4/1996 | Buffaloe, IV et al. |
| 5,570,026 A | 10/1996 | Buffaloe, IV et al. |
| 5,601,080 A | 2/1997 | Oppenheimer |
| 6,041,246 A | 3/2000 | Krivitski et al. |
| 6,117,099 A * | 9/2000 | Steuer et al. .................. 604/4 |
| 6,493,567 B1 | 12/2002 | Krivitski et al. |

* cited by examiner

*Primary Examiner*—Eric F. Winakur
(74) *Attorney, Agent, or Firm*—Brian B. Shaw; Stephen B. Salai; Harter, Secrest & Emery LLP

(57) ABSTRACT

A method and device for the continuous real-time monitoring of relative blood volume change, based on registration of blood hemoglobin concentration, during long periods of time, such as dialysis session. A method and device for cardiac output measurement during dialysis, surgeries, intensive care procedure is provided. Calibration of a sensor in response to a change in a measureable blood property is determined from a coefficient corresponding to a change in the measured blood property.

8 Claims, 5 Drawing Sheets

Not compensated for sodium content signals

Not compensated for flow effect signals

Scatter Diagrams

Particular direction scatter diagrams

Principal dependence of absolute relative error of blood optical density measurement on an angle between Illumination Vector and Detection Vector Compensated for scattering caused by sodium content signals Compensated for scattering caused by flow effect signals

SENSOR CALIBRATION AND BLOOD VOLUME DETERMINATION

The present application claims priority as a continuation in part of U.S. Ser. No. 09/528,880 filed Mar. 20, 2000, now U.S. Pat. No. 6,493,567, which is a divisional of U.S. Ser. No. 08/950,244 filed Oct. 14, 1997 now U.S. Pat. No. 6,041,246, each of which is hereby expressly incorporated by reference.

FIELD OF THE INVENTION

The present invention relates to the photometric analysis of blood properties to monitor changes in blood volume, blood proteins concentration, cardiac output and other hemodynamic parameters. More particularly, the invention includes a method and apparatus for employing a single light emitter and a single photodetector, the single photodetector is oriented with respect to the emitter to minimize a scattering effect of the light from the electrolyte composition of the blood, blood flow rate, blood hematocrit level and other factors.

BACKGROUND OF THE INVENTION

The optical density of blood corresponds to a number of factors and the measurement of the optical density of the blood has been used to determine certain blood parameters.

For example, during a hemodialysis session when fluid is being removed from the blood stream by a dialyzing machine, the concentration of hemoglobin, naturally occurring in the red blood cells, may decrease or, generally increase, with respect to the equilibrium processes of the fluid removal and mobilization from the body tissues. The change in the concentration of hemoglobin results in a corresponding change in the optical density of the blood and may be registered.

Monitoring changes in blood volume, as well as blood hemoglobin, can help to prevent such complications as hypotension due to continuous hypovolemia. Cardiac output of a patient, as well as other hemodynamic parameters of cardiovascular system, also provide useful information about the patient condition during hemodialysis, surgery, and in intensive care units. Using a dilution technique it is possible to calculate several characteristics of cardiovascular system, particularly cardiac output.

There are several research works and patents in the field of photometric blood monitoring. As shown in U.S. Pat. No. 3,830,569 to Meric; U.S. Pat. No. 4,243,883 to Schwartzmann; and U.S. Pat. No. 4,303,336 to Cullis, a device with suitable light source and photodetector may be used. Multiple detectors may be used, as shown by Meric.

As illustrated by U.S. Pat. No. 4,745,279 to Karkar et al.; U.S. Pat. No. 4,776,340 to Moran et al.; U.S. Pat. No. 5,048,524 to Bailey; and U.S. Pat. No. 5,066,859 to Karkar, additional detectors may be used to compensate various measurement artifacts, particularly for variations in intensity of light entering the blood stream.

However, the correlation between blood parameters and data obtained by photometric methods needs to be enhanced.

In U.S. Pat. No. 5,331,958 to Oppenheimer, a through photodetector and a remote photodetector are used for correction of light scattering due to sodium concentration fluctuations in the blood. Signals of the through and the remote photodetector are amplified separately. The data from the remote detector is used to compensate or adjust the data of the through detector. These and other dual correction or compensation systems are subject to the inherent unreliability of multiple detectors, as well as calibration issues.

A disadvantage of other methods of photometric analysis of blood properties, which utilize conventional external tubing, includes a dependence on the physical characteristics of the tubing such as diameter, wall thickness, and light absorption factor.

Therefore, the need exists for a method and apparatus which require only a single light detector, wherein the light scattering effect is eliminated or minimized. In such an apparatus, the mechanical construction and data collection process is substantially streamlined as compared to multiple photodetector devices. There is a need for a method and apparatus having automatic calibration of the optical probe sensitivity for each particular tubing that the probe is employed with; and further having a dilution technique applicable for determining hemodynamic parameters of a patient.

SUMMARY OF THE INVENTION

In accordance with the present invention, there is a novel method and apparatus for the photometric analysis of blood properties. The present design allows for registration of blood optical density, provides signal adjustment for fluctuations in light scattering, which are related to blood electrolyte composition, as well as blood flow rate and other blood parameters.

The present apparatus employs a single light emitter projecting a light beam along an illumination axis and a single receiving photodetector for measuring light along a detection axis, wherein the illumination axis is non colinear, offset or angled with respect to the detection axis. According to the method, the present invention includes projecting a light beam into a blood column along an illumination axis, and detecting the light emerging from the blood column by a single receiving photodetector receiving system along a detection axis that is non colinear to the illumination axis.

The effects of light scattering are taken into consideration and have been eliminated by the location and orientation of the single receiving photodetector detection axis with respect to the illumination axis. It is understood the present system may be employed with additional sensors or detectors, however these sensors are not required, or related to the light scattering compensation, but are employed for different purposes.

Preferably a light emitter of isobestic wavelength is used to avoid the effect of hemoglobin oxygen saturation.

The device may be used with an extracorporeal tubing system through which blood flows, as well as being applied to patient' vessels and body tissues which are capable of being transilluminated. Further, the device may be used during a dialysis session as well as surgeries, intensive care procedures, measurements hemodynamic parameters of blood by dilution technique, or other blood property altering events.

The present method includes utilizing biologically natural indicators, as for example isotonic saline, glucose, or another solution, for measurements by dilution technique and calibration procedures. There is no need in special markers, such as dye-green or the like, which stay in a patient's body for a long time.

In the drawings and in the detailed description of the invention there are shown and described only principal embodiments of this invention and are of illustrative nature only, but not restrictive. Other embodiments and technical realizations are applicable, all without departing from the scope and spirit of the invention.

DETAILED DESCRIPTION OF THE PREFERRED EMBODIMENTS

Figure 1:
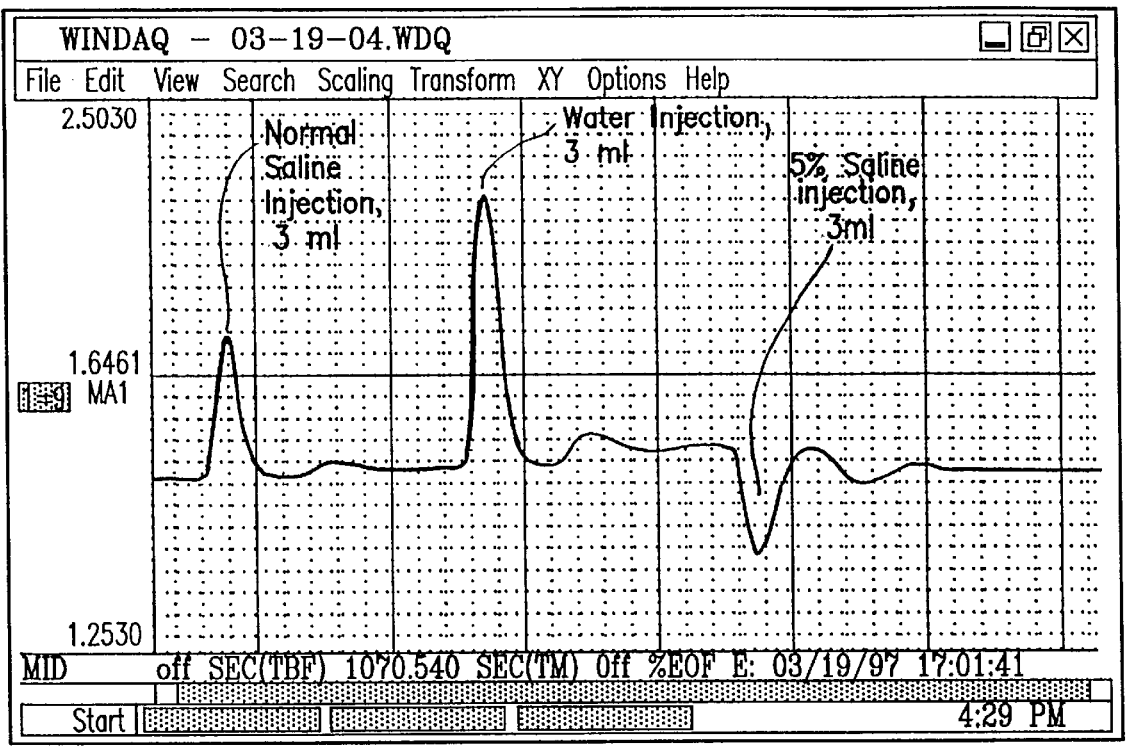
FIG. 1 is a plot showing the light intensity changes caused by equal diluting volumes of isotonic saline, water and hypertonic saline.

Generally, the present method and apparatus include a probe 10 having a housing 20, a light source 30 and a receiving photodetector 40 for cooperating with a length of light transmissive tube 50.

The light transmissive tube 50 may be any of a variety of conduits including but not limited to a dialysis tubing system, an artery-vein extracorporeal tubing shunt, or blood vessel.

The housing 20 is sized to operably retain the light source 30 and the photodetector 40. The housing 20 includes a light port 22 through light from the light source 30 may pass. The housing 20 includes a tube receiving passage 24 for receiving a length of the light transmissive tube 50, wherein which blood may flow through the tube. The housing 20 is constructed to dispose the tube 50 intermediate the light port 22 and the photodetector 40.

Figure 7:
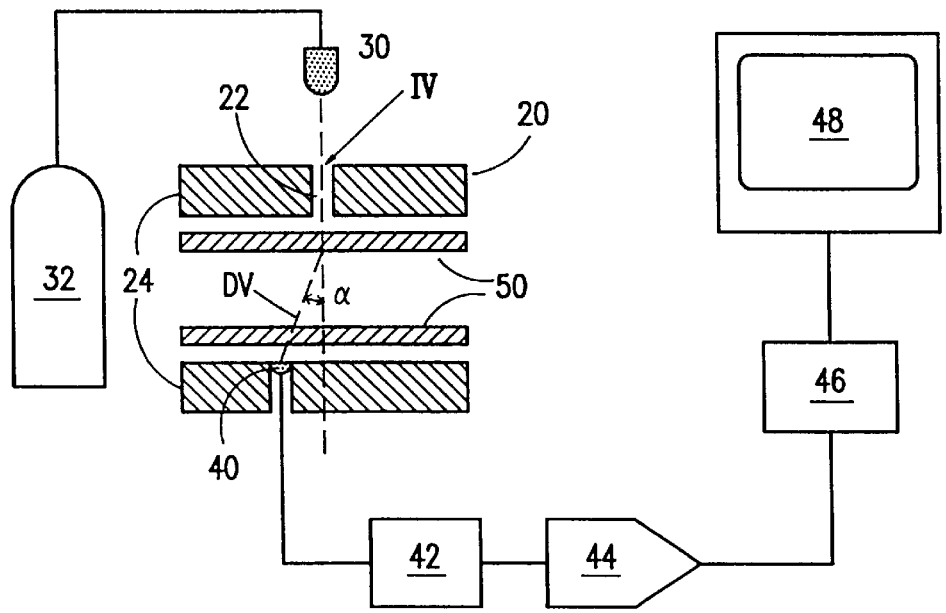
FIG. 7 is a schematic of the present single emitter-single detector system.

Referring to FIG. 7, the probe 10 embodying the present apparatus is shown in an illustrative form. The probe 10 includes the light source 30 for generating a light beam. The generated light beam travels along an illumination vector IV. The illumination vector IV of the light may be dictated by the light source 30 itself, or by the configuration of the housing 20. Specifically, the light port 22 of the housing 20 may be configured as a slit or aperture through which light from the light source 30 passes, and the housing thus permits only light passing along a predetermined illumination vector IV to intersect the tubing 50. As shown in FIG. 7, in a first embodiment the light source 30 and housing 20 produce an illumination vector that is perpendicular to a longitudinal axis of the tubing 50.

To avoid the need in correction for oxygen saturation, a light source 30 with an isobestic wavelength of emission spectrum may be used. The light source 30 is driven by light source driver 32. The light source driver 32 may include optical feedback for source of supplied current, or may be a dedicated laser diode driver.

The receiving photodetector 40 is spaced from the light port 22 to locate a length of the light transmissive tube 50 therebetween. The receiving photodetector 40 is constructed to detect an intersection of light along a detection vector DV. As blood flows through the tube 50, a blood column is exposed to the illumination vector IV and the photodetector 40. Light initially entering the blood column along the illumination vector IV is absorbed and scattered in the blood flowing through the tubing 50. The receiving photodetector 40 is oriented to receive only that part of the light passing through and emerging from the blood column that is scattered by the angle α with respect to the illumination vector IV. Thus, only light that is inclined from the illumination vector IV by the angle α reaches the receiving photodetector 40. The detection vector DV of the receiving photodetector 40 is offset from the illumination vector IV by the angle α, thereby allowing only light scattered by angle α to reach the receiving photodetector. That is, the detection vector DV is inclined with respect to the illumination vector IV by the angle α. Although the receiving photodetector 40 is shown as coincident with the detector port, it is understood the detector port may define the interface with the blood column wherein the receiving photodetector is spaced from the blood column. That is, the application of secondary optics may allow the light source 30 to be spaced from the light port 22 and the receiving photodetector 40 to be spaced from the detector port.

Therefore, in the present design light is projected along a linear illumination vector IV and the detection vector DV of the receiving photodetector 40 is offset from the illumination vector by the angle α such that only light scattered by the angle α intersects the receiving photodetector.

The signal detected by the receiving photodetector 40 is amplified by an amplifier 42 to produce an amplified signal. The amplifier 42 may apply a logarithmic transformation function to be able to further operate in terms of optical density of the blood rather than merely detected light intensity. Conveniently, the amplified signal is applied to an analog-to-digital converter 44, and passes into a microprocessor interface 46. After processing the amplified and digitized signal to produce data, the microprocessor interface 46 causes the data to appear at a conventional monitor 48, such as a computer.

Figure 8:
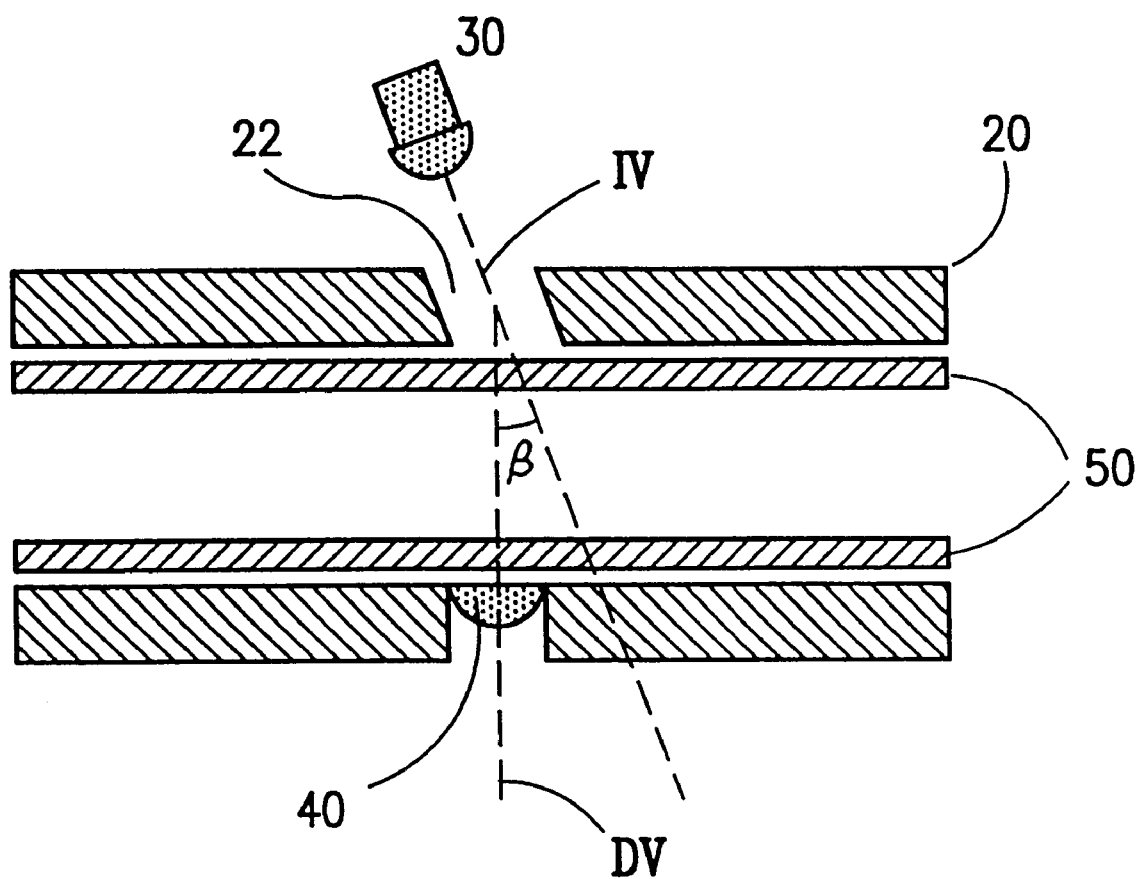
FIG. 8 is a schematic of an alternative embodiment of the present single emitter-single detector system.

An alternative embodiment of the optical probe 10 is shown in FIG. 8. In this embodiment, the relative orientation between the light source 30 and the receiving detector 40 is modified. However, the illumination vector IV remains offset from the detection vector DV by the angle β. It is understood that the angle between the illumination vector IV and the detection vector DV, shown as α in FIG. 7 and β in FIG. 8 may not be identical. While the angles β and β could be equal, they may vary depending upon the specific configuration of the system.

As shown in FIG. 8, the probe 10 is constructed so that the housing 20 locates the light source 30 straight across from a receiving detector 40. That is, the light port 22 and the photodetector 40 are located at the same longitudinal position along the tubing 50, and are perpendicular to a longitudinal axis of the length of tubing as the tubing passes through the housing 20. In this configuration, the illumination vector IV is non perpendicular to the longitudinal axis of the tubing 50. That is, the illumination vector IV includes a component that extends along the longitudinal axis of the local length of the tubing 50 and hence blood column. In this configuration, the angle between the illumination vector IV and the detection vector DV is β. Locating the photodetector 40 and detection vector DV at the angle β from the illumination vector IV results in the photodetector registering the same portion of scattered light as the first configuration.

It is understood that some accommodation may be made for the defraction of the light as the light passes from the air through a wall of the tubing 50, into the blood, from the blood into a second wall of the tubing and from the tubing into the air. However, it is believed such accommodation is relatively small and may be accounted for by a small shift in alignment of housing to correct diffraction by parallel layers of materials.

Theory

Figure 2:
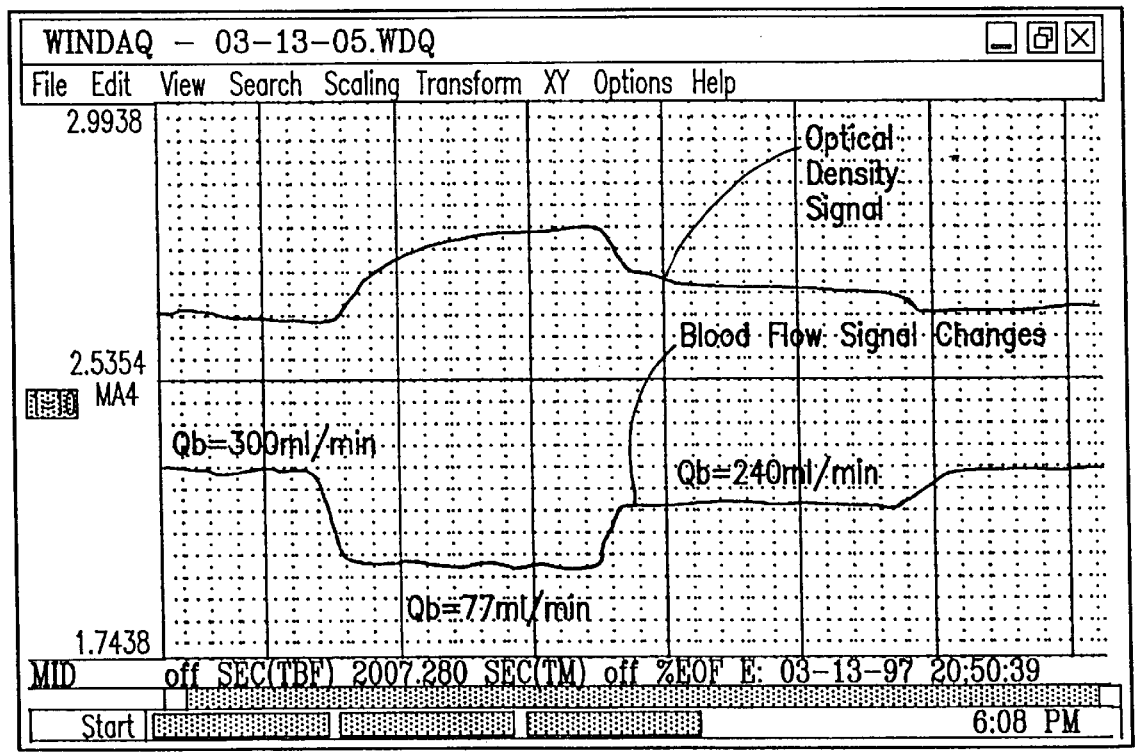
FIG. 2 is a plot showing the light intensity changes caused by the blood flow rate changes.
Figure 3:
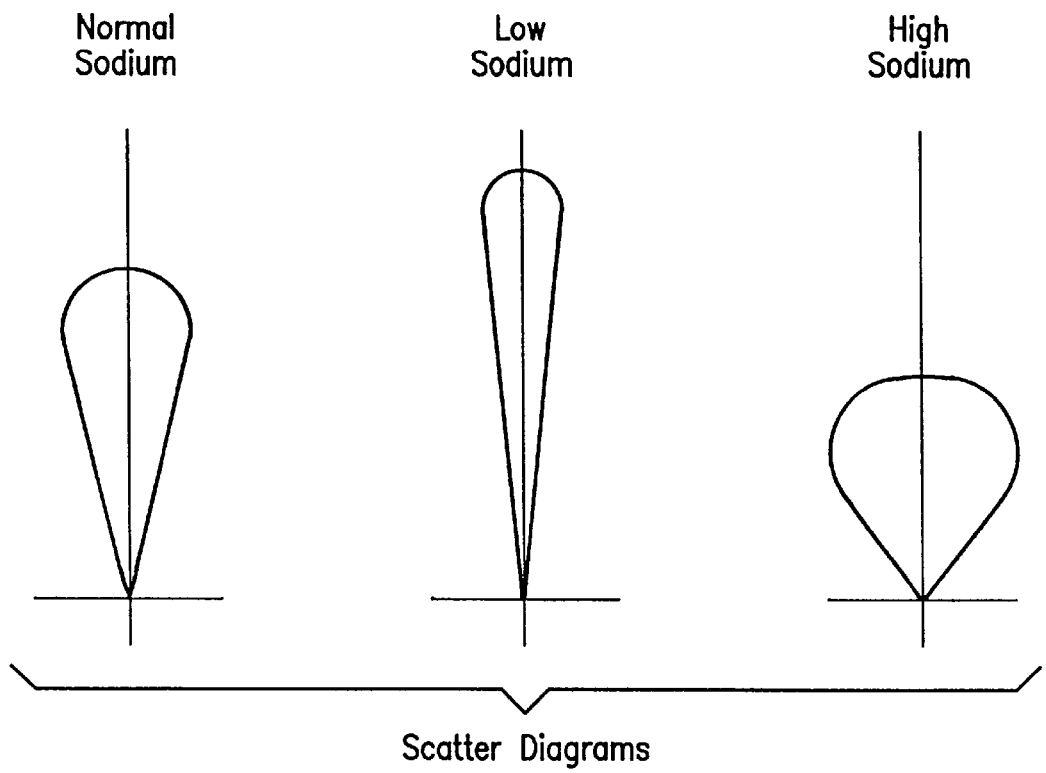
FIG. 3 is a diagram showing the light scattering dependence on hematocrit level, blood electrolytes and blood flow rate.

As stated, a change in hemoglobin concentration induces a change in the optical density of blood. An amount of light passing through a blood sample and emerging from the blood sample can be disposed and interpreted to determine blood properties. However, there are several factors that influence light scattering in blood. These factors include electrolyte composition, flow rate and hematocrit level of the blood. These influences introduce error in hemoglobin evaluation as well as injection bolus registration measurements made by a photodetector and light source having aligned illumination vectors and detection vector (that is, the detector is displaced straightway across the tubing from the light source at a common longitudinal position and illumination vector is collinear with the detection vector). Thus, in the systems of the prior art, the illumination vector and the detection vector are colinear. These influences are conveniently referred to as the "scatter effect" and are illustrated in FIGS. 1, 2 and 3.

Figure 4A:
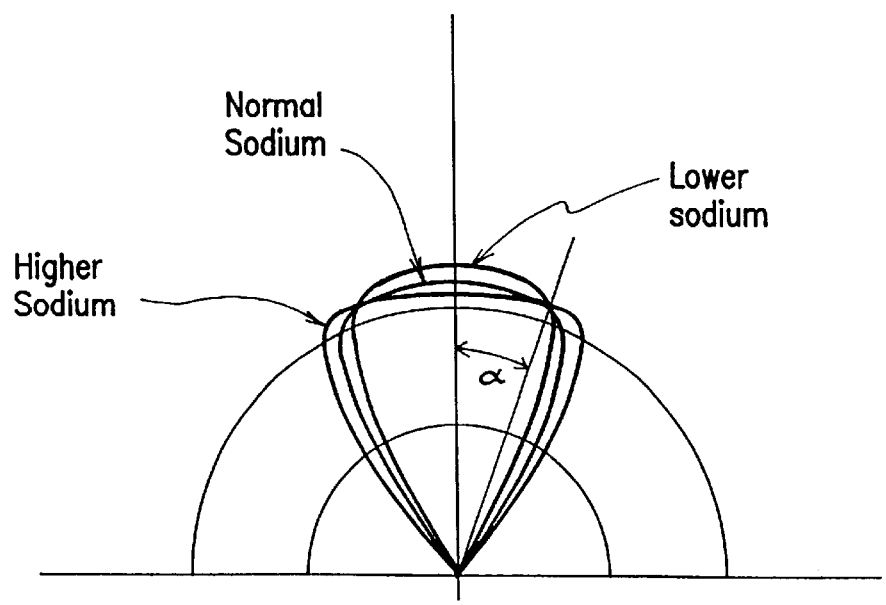
FIG. 4a is a diagram showing a particular angle α in an emitted light beam that is characterized by stable light portion.

Referring to FIG. 4*a*, as it has now been discovered, there is a particular angle α between the illumination vector IV of an emitted beam and a detection vector DV which is characterized by stable light portion, scattered in this direction. For fixed distance between a light source (distance from the light port 22 to the receiving photodetector 40), fixed blood column width and stable emitted light intensity, the signal received by the receiving photodetector at the angle α from the illumination vector IV is a function of hemoglobin concentration of blood and does not depend on light scattering.

Figure 4B:
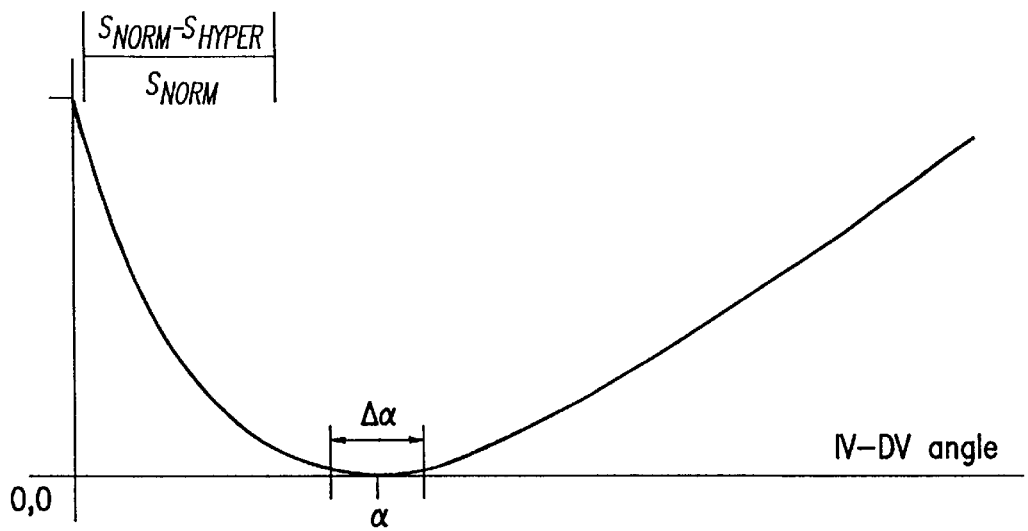
FIG. 4b is a diagram showing a principal dependence of absolute relative error of blood optical density measurement on an angle between Illumination Vector (IV) and Detection Vector (DV), where $S_{NORM}$ is signal change while electrolyte composition remains unchanged, $S_{HYPER}$ is signal change when electrolyte content was increased. An angle a is the angle of zero error, and still some vicinity Δα is a range of angles where accuracy of measurement remains acceptable.
Figure 5:
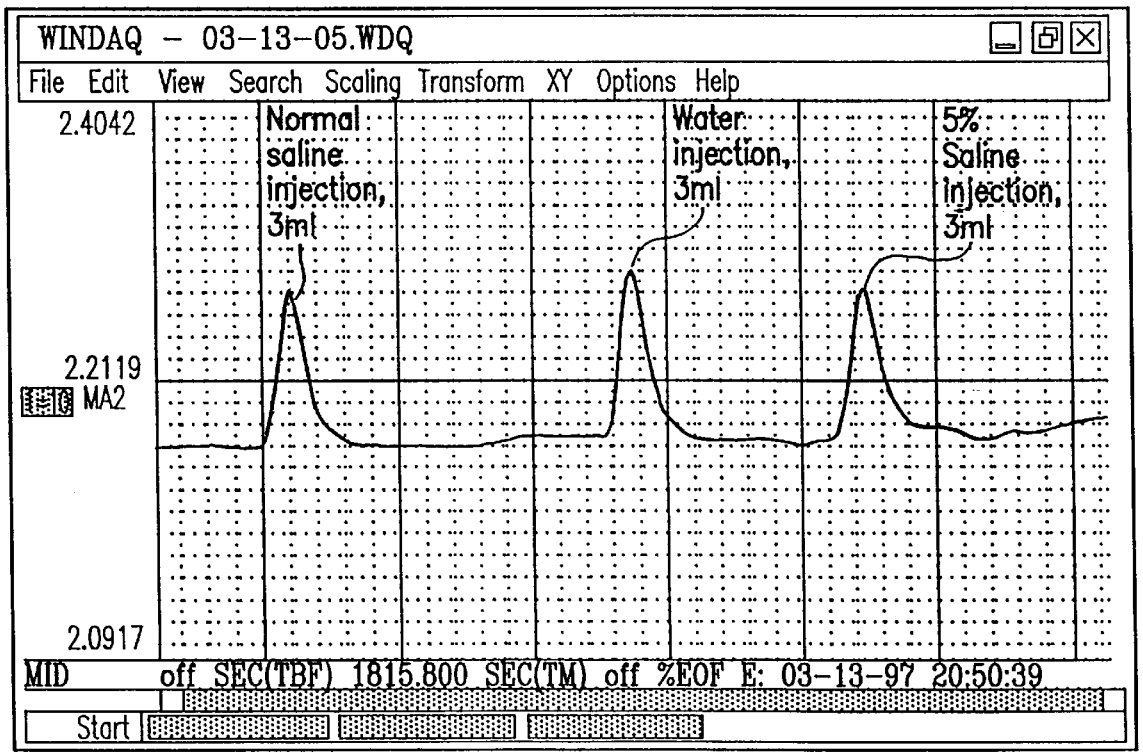
FIG. 5 is a plot showing registered light intensity signals for three bolus injections of equal volume of normal saline, water and 5% saline with a sensor constructed and located to adjust for the scattering effect.
Figure 6:
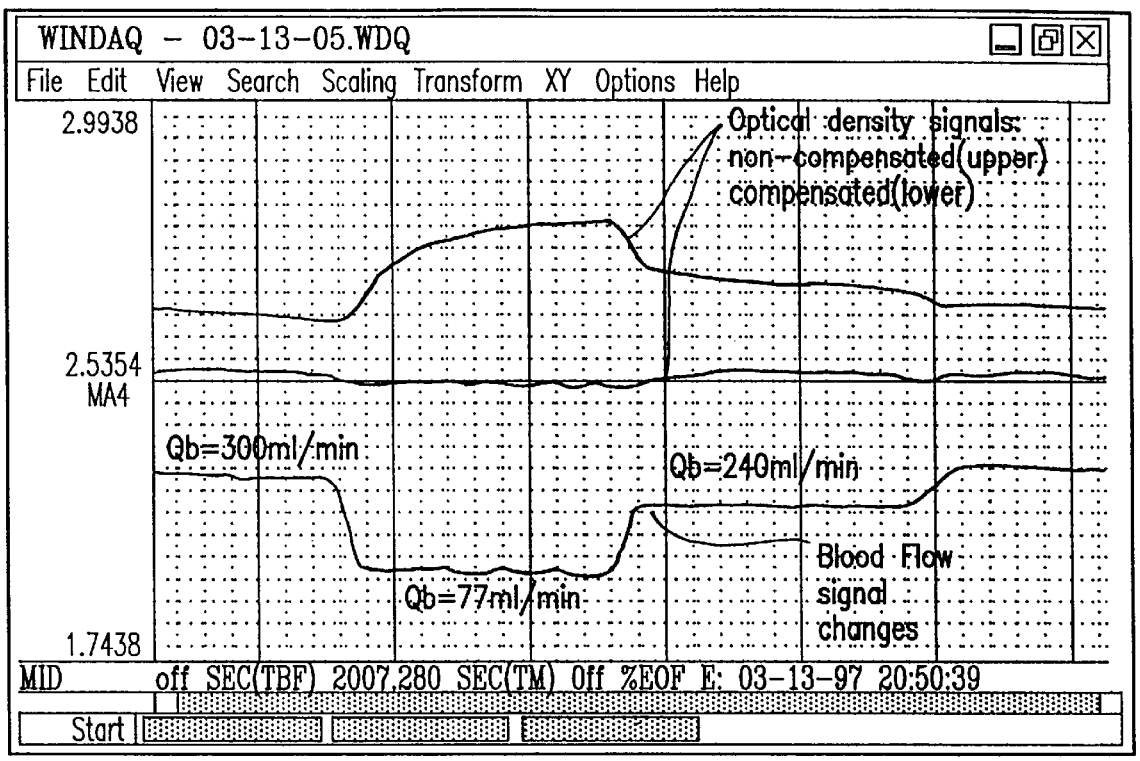
FIG. 6 is a plot showing the light intensity changes caused by the blood flow rate changes registered with a sensor constructed and located to adjust for the scattering effect (lower trace) versus changes registered with traditional straight transilluminating sensor (upper trace).

Based on this understanding, the present optical probe 10 was designed. For this probe 10, the scatter effect is essentially eliminated due to selection of adequate angle as illustrated in FIG. 4*b*. Registered detected light intensity signals for three bolus injections of equal volume of normal saline, water, and 5% saline are shown in FIG. 5. Blood flow related signals, shown in FIG. 6, also represents substantial improvement.

Signal Processing

Signal processing for the evaluation of the blood optical properties, changes in liquid balance of the blood and cardiac output calculation are based on following:

Assuming the number of erythrocytes remains constant during blood dialyzing, changes in liquid content induce changes in blood hemoglobin concentration. Relative volume change can be expressed as:

$$\frac{\Delta V}{V_0} = \left(1 - \frac{C_0}{C}\right) \quad \text{(Equation 1)}$$

where $C_0$ is the initial, or basic hemoglobin concentration; C is the current hemoglobin concentration; $V_0$ is the initial volume and $\Delta V$ is the change in volume. Concentration can be evaluated from knowing the amount of light emerged from the blood by applying Beer-Lambert Law:

$$I = I_s e^{-kch} \quad \text{(Equation 2)}$$

where I is intensity of light being absorbed emerging from the blood column of a thickness h; $I_s$ is light intensity of the light source; k is the absorption coefficient; and C is concentration of the medium. Relative volume change can be expressed through the light intensity as:

$$\frac{\Delta V}{V_0} = \left(1 - \frac{\ln\frac{I_s}{I_0}}{\ln\frac{I_s}{I}}\right) \quad \text{(Equation 3)}$$

where $I_S$ is light intensity of the light beam; $I_0$ is the intensity of emerged light for initial concentration of blood hemoglobin and I is the intensity of emerged light for current meaning of concentration.

Relative hemoglobin concentration change can be expressed through the light intensity as:

$$\frac{\Delta C}{C_0} = \left(1 - \frac{\ln\frac{I}{I_0}}{\ln\frac{I_s}{I_0}}\right) \quad \text{(Equation 4)}$$

An important parameter of the system is the sensitivity of the probe 10. Different brands of tubing 50, even different sections of tubing of the same brand may have different diameters and wall thickness. An absorption factor of the tubing material can also vary. Thus, sensitivity of the probe 10 should be known or determined for every particular tubing sample. It is also important to know any possible change in sensitivity of the probe 10 over relatively long periods of monitoring the blood properties.

A registered change in the optical signal received by the photodetector 40 is proportional to a relative concentration change, $$\frac{\Delta C}{C_0},$$

with a proportion coefficient, (a factor for sensitivity of the optical probe 10 to relative blood hemoglobin concentration change), K:

$$\frac{\Delta C}{C_0} = K \cdot \Delta U \quad \text{(Equation 5)}$$

where $\Delta U$ is the change in the optical signal received by the photodetector 40, measured in volts, for example. To determine K, a known change is made in the relative hemoglobin concentrations and a corresponding signal change $\Delta U$ is registered.

Calibration

To provide correct data registering during long term monitoring of blood properties, measurements of hemodynamic parameters by dilution technique, and determining different absolute blood parameters, an optical sensor should be calibrated for particular operating conditions, such a current tubing system, initial blood parameters, as well as environmental changes occurring over the duration of the measurements.

When conventional hemodialysis is conducted, there are two major ways to calibrate the system. The calibration includes producing a known change in a blood optical property and registering the corresponding change in the measured (detected) signal.

In a first, more preferable method, the probe 10 is placed on the venous side of the dialysis tubing system, downstream from the dialyzer. In the first method of calibration, the ultrafiltration rate is changed by a known amount, or completely terminated. When the ultrafiltration rate is altered, the venous flow rate becomes greater by ultrafiltration rate change $Q_{UF}$. The change in the ultrafiltration rate produces a decreasing hemoglobin concentration.

Relative concentration changes in a venous line can be expressed through blood flow rates as follows:

$$\left.\frac{\Delta C}{C_0}\right|_V = -\frac{Q_{UF}}{Q_B} \qquad \text{(Equation 6)}$$

where $Q_B$ is the known blood flow rate in an arterial side and $Q_{UF}$ is the known ultrafiltration rate change. Thus, desired coefficient K is:

$$K = -\frac{Q_{UF}}{Q_B} * \Delta U_{UF} \qquad \text{(Equation 7)}$$

where $\Delta U_{UF}$ is change in the detected registered signal as caused by the change in the ultrafiltration rate.

The relative change in hemoglobin concentration of the arterial blood is calculated through a measured venous side concentration change according to:

$$\left.\frac{\Delta C}{C_0}\right|_{AR} = \left(1 - \frac{Q_{UF}}{Q_B}\right)\left.\frac{\Delta C}{C_0}\right|_V \qquad \text{(Equation 9)}$$

where $$\left.\frac{\Delta C}{C_0}\right|_{AR}$$

is the relative change in arterial hemoglobin concentration, $$\left.\frac{\Delta C}{C_0}\right|_V$$

is the relative change in venous hemoglobin concentration, $Q_{UF}$ is ultrafiltration rate, and $Q_B$ is blood flow rate in the arterial side.

Dialysis machines of some brands turn ultrafiltration off during dialysis session several times to conduct internal self-calibration. Advantageously, these self-calibrating procedures can be used for calibration of the sensitivity optical probe to the relative concentration change.

Another method of calibrating the sensitivity of the probe is to employ an indicator which dilutes the photometric density of the blood passing through the tubing 50. For example, an injection of an indicator, such as normal saline or another conventional solution, is made into an injection port of the dialysis system. The indicator injection should be made upstream from the probe 10, so that all the indicator passes through the probe between the light port 22 and the photodetector 40. The indicator injection causes the optical property of the blood to change, thus changing the light intersecting the photodetector 40 along the detection vector. The change in the amount of detected scattered light is registered by the probe 10, and specifically the photodetector 40. Coefficient K can then be calculated through the volumes:

$$K = -\frac{V_{Inj}}{V + V_{Inj}} * \Delta U_{Inj} \qquad \text{(Equation 8)}$$

where $V_{Inj}$ is injection's volume; $V=(Q_B-Q_{UF})*\Delta T_{Inj}$, $\Delta T_{Inj}$ is the transit time of the injection bolus; and $\Delta U_{Inj}$ is integrated over $\Delta T_{Inj}$ registered signal change.

The calibration can also be made with the routine injection of a dilution indicator into an injection port on an arterial side of the dialysis system. The probe 10 is then placed on arterial side, downstream from the place of injection. Again, all the injected indicator must pass through the probe 10. No recalculation is required in this case.

A calculation of cardiac output (CO) of a patient can be made by dilution techniques with the following method.

By injecting a known amount of an indicator into a blood flow, the diluting effect of the indicator over a period of time can be accurately determined by a sensor responsive to changes of photometric properties of the blood. The sensor is positioned so that the indicator passes the sensor, with the measured diluting effect being used to determine various blood parameters. The measurement may be made in an extracorporeal blood system in which optical measuring probes are secured, for example, to tubing leading to exterior blood treatment equipment such as hemodialysis machine, extracorporeal artery-vein passive shunt, or the like. Thereafter, a bolus, or known volume, of an indicator material is injected into the bloodstream, and measurements are made of changes in the photometric properties of the blood to determine the passage of the bolus past the optical probe 10. The changes in such photometric properties of the blood can then be plotted and used to determine various hemodynamic parameters, particularly cardiac output of a patient.

With the aim of calibration for optical properties of different tubing, the above mentioned calibration injection of known amount of an indicator may be employed. The calibration injection must be made directly prior to the location of the probe, while simultaneously measuring the blood flow through the blood system. A blood flow measuring device can be, for example, ultrasonic flow meter such as those manufactured by Transonic Systems, Inc., Ithaca, N.Y. The cardiac output will be calculated as follows:

$$CO = \frac{V_{ind} \cdot S_{cal-ind}}{V_{cal-ind} \cdot S_{b-ind}} \cdot Q_{A-cal} \qquad \text{(Equation 13)}$$

where $V_{cal-ind}$ is the volume of the calibrating injection, $S_{cal-ind}$ is the dilution area under a curve generated by the measurement of dilution produced by a calibrating injection.

Generally, cardiac output of a patient's heart may by calculated as:

$$CO = \frac{K_s \cdot V_{ind}}{S_{b-ind}} \quad \text{(Equation 14)}$$

where $V_{ind}$ is total volume of injected indicator; $S_{b-ind}$ is the area under a dilution curve representing the total optical density changes in the blood column over a time period; and $K_s$ is the calibration coefficient for a particular set of tubing and probe, as determined earlier.

As an advantage of using the probe for cardiac output measurement, it should be noted the insensitivity of the probe to temperature variations in blood, indicator, and the tubing carrying the blood. Further, since the probe can be secured in extracorporeal tubing system such as passive arterial-venous shunt or dialysis tubing, the present method of cardiac output measurement substantially reduces the invasive penetration into a patient's vital organs, such as the heart, as compared to Swan-Ganz catheter.

It is understood the same calibration approach, including using a change in ultrafiltration rate or indicator injection can be used for sensors other than optical sensors, wherein these alternative sensors can provide a signal corresponding to any of a variety of measureable blood parameters or properties including, but not limited to protein concentration, saline, electrolytes or any other measurable blood property or parameters.

Therefore, any type of optical sensor, impedance, resistance or electrical sensors which measure a changeable blood parameter such as the sound or ultrasound velocity in blood can be calibrated. Electrical resistance of the blood can be measured, as the resistance depends on the volume of red blood cells (hematocrit). Calibration can be provided for ultrasound velocity sensors, as well as temperature sensors and optical density, density or electrical impedance sensors can be used to detect changes in blood parameters.

A known change in the ultrafiltration rate will produce a corresponding measurable change in ultrasound velocity in the blood or if electrical resistance is measured, a voltage proportional to the ultrasound velocity. For example, having an initial venous blood flow $Q_b$=300 ml/min, then after initiating ultrafiltration rate of $Q_f$=30 ml/min. is filtered out, the resulting change in concentration of large particles that were not withdrawn in the dialyzer (proteins, hematocrit) in the remaining flow 270 ml/min will be 100 (30 mil/min/300 ml/min)=10%.

Thus, if in this example, the change in voltage of the ultrasound sensor was 5 volts, the resulting correspondence provides that each 1 volt change will represent 10%/5 volts or a 2% volume change. Thus, k=2%/1 volt. As set forth above the blood volume can then be determined.

While a preferred embodiment of the invention has been shown and described with particularity, it will be appreciated that various changes and modifications may suggest themselves to one having ordinary skill in the art upon being apprised of the present invention. It is intended to encompass all such changes and modifications as fall within the scope and spirit of the appended claims.

What is claimed is:

1. A method for measuring a blood volume change, the method comprising:
    (a) connecting an arterial tubing portion of a dialysis system to withdraw blood from a patient and connecting a venous tubing portion of the dialysis system to deliver filtered blood to the patient;
    (b) operably coupling an optical sensor to the venous tubing portion of the dialysis system;
    (c) changing an ultrafiltration rate of the dialysis system;
    (d) determining at least one photometric property of blood at the venous tubing portion of dialysis system;
    (e) determining a calibration coefficient of at least the optical sensor; and
    (f) determining a blood volume change corresponding to the calibration coefficient.

2. The method of claim 1, wherein changing the ultrafiltration rate includes changing the ultrafiltration rate by a known amount.

3. The method of claim 1, wherein changing the ultrafiltration rate includes temporarily stopping the ultrafiltration.

4. The method of claim 1, wherein determining the at least one photometric property of blood includes determining a property corresponding to a protein in the blood.

5. The method of claim 1, wherein determining the at least one photometric property of blood includes determining a property corresponding to a protein concentration in the blood.

6. The method of claim 1, wherein determining the at least one photometric property of blood includes determining a property corresponding to a hematocrit of the blood.

7. The method of claim 1, wherein determining the at least one photometric property of blood includes determining a property corresponding to red blood cells in the blood.

8. The method of claim 1, wherein determining the at least one photometric property of blood includes determining a property corresponding to an optical density of the blood.

* * * * *